United States Patent [19]

Kusatsu et al.

[11] Patent Number: 5,795,979
[45] Date of Patent: Aug. 18, 1998

[54] WATER-INSOLUBLE GLUCAN PURIFICATION METHOD

[75] Inventors: Masayoshi Kusatsu; Tetsuo Tanegawa; Shigeyoshi Miyashiro, all of Saga, Japan

[73] Assignee: Ajinomoto Co., Inc., Tokyo, Japan

[21] Appl. No.: 867,354

[22] Filed: Jun. 2, 1997

[30] Foreign Application Priority Data

Jun. 6, 1996 [JP] Japan ..................... 8-144126

[51] Int. Cl.$^6$ ............... C07H 1/00; C07H 1/06; C08B 37/00
[52] U.S. Cl. .............. 536/123.12; 536/124; 536/127
[58] Field of Search .................. 536/123.12, 124, 536/127

[56] References Cited

U.S. PATENT DOCUMENTS

| | | | |
|---|---|---|---|
| 4,072,567 | 2/1978 | Yokobayashi et al. | 536/123.12 |
| 4,908,310 | 3/1990 | Clarence S. Buller | 536/114 |
| 5,223,491 | 6/1993 | Byron A. Donzis | 514/54 |

OTHER PUBLICATIONS

Chemical Abstracts, vol. 83, No. 18, p. 90, 1975, AN–148908m, M. Egamberdyev, et al., "Preparation of High–Quality Cotton Cellulose for Rayon Production".

Journal of Cereal Science, vol. 13, No. 3, pp. 275–290, 1991, H. Gruppen, et al., "Barium Hydroxide As A Tool To Extract Pure Arabinoxylans From Water–Insoluble Cell Wall Material of Wheat Flour".

*Primary Examiner*—John Kight
*Assistant Examiner*—Everett White
*Attorney, Agent, or Firm*—Oblon, Spivak, McClelland, Maier & Neustadt, P. C.

[57] ABSTRACT

The present invention relates to a water-insoluble glucan purification method characterized in that a culture solution of a microbe that produces water-insoluble glucan or a microbial cell-containing solution comprising water-insoluble glucan as a component is treated with both an oxide of 0.175–3.5 wt.—wt. % and a hydroxide such that the pH value becomes 10–12.5. Since the present invention accomplishes all of the destruction of production microbe, the decolorization and the reduction of viscosity of a culture solution of a microbe that produces water-insoluble glucan or a microbe cell-containing solution comprising water-insoluble glucan as a component, the invention purifies water-insoluble glucan industrially at low costs and with a high efficiency.

4 Claims, No Drawings

WATER-INSOLUBLE GLUCAN PURIFICATION METHOD

BACKGROUND OF THE INVENTION

1. Field of the Invention

The present invention relates to a method for purifying water-insoluble glucan from a culture fluid of a microbe that produces water-insoluble glucan or a microbial cell-containing solution comprising water-insoluble glucan as a component.

2. Description of the Prior Art

Water-insoluble glucan is used as natural fiber in food material (Japanese Patent Laid-Open No. Sho 60-105460, Japanese Patent Laid-Open No. Sho 62-83854), artificial skin (Fontana et al., Applied Biochemistry and Biotechnology, vol.24/25, P.253–264, 1990), paper making (Japanese Patent Laid-Open No. Sho 63-295793), an anti-tumor agent (Japanese Patent Publication No. Sho 40-22398, Japanese Patent Publication No. Sho 47-37002).

Water-insoluble glucan can be obtained through ventilated-stirred culture, stationary culture, solid culture of acid bacteria, Basidiomycetes, yeast or the like. However, since the culture fluid contains impurities originating from the culture components, low or high-molecular impurities produced by culturing the production microbe, it is necessary to separate, fractionate and purify water-insoluble glucan from such impurities. The purification is performed by a normal method for purifying polysaccharide, and the removal of impurities is performed by, for example, centrifugal separation, extraction using an acidic or alkaline solution or hot water, precipitation using an organic solvent, dialysis, ion-exchange chromatography (Japanese Patent Publication No. Sho 42-2918), a method that removes impurities by precipitating them as quaternary ammonium salts (Japanese Patent Publication No. Sho 43-20567), a method that performs fractional precipitation of quaternary ammonium compounds in a specific pH range (Japanese Patent Publication No. Sho 47-37002), and the like. There are other problems with the culture solution, that is, increases in viscosity, residual production microbe, coloring and the like, which impede the solid-liquid separation and causes impurities or water-insoluble glucan to remain in targeted material during filtration. Thus, the purification of water-insoluble glucan from a culture solution requires complicated steps, such as removal of coloring substances (Japanese Patent Publication No. Sho 53-44563) or removal of high-molecular substances, in addition to removal of impurities, according to the conventional art.

OBJECTS AND SUMMARY OF THE INVENTION

It is an object of the present invention to provide a water-insoluble glucan purification method that does not require a complicated step and is low cost and efficient on an industrial scale.

The present inventors considered that an improvement in the liquid properties of the culture solution of a water-insoluble glucan producing microbe or the microbial cell-containing solution comprising water-insoluble glucan as a component was important for efficient purification of water-insoluble glucan from the solution. Through researches, the inventors have found that treatment of the solution with both a hydroxide and an oxide will achieve all of destruction of the production microbe cells, decolorization and a reduction in viscosity, and enable efficient purification of water-insoluble glucan, thus achieving the present invention.

Accordingly, the present invention is a water-insoluble glucan purification method characterized in that a culture solution of a microbe that produces water-insoluble glucan or a microbial cell-containing solution comprising water-insoluble glucan as a component is treated with both an oxide of 0.175–3.5 wt.—wt. % and a hydroxide such that the pH value becomes 10–12.5.

The present invention will be described in detail below.

DETAILED DESCRIPTION OF THE INVENTION

Specific examples of water-insoluble glucan, that is, an object substance of the purification method of the present invention, are bacterial cellulose produced by acetic acid bacteria, lenthinan, which is a constituting component of Basidiomycete, yeast glucan, which is a surface structure of yeast, and the like.

The water-insoluble glucan producing or constituting microbe used by the present invention is not particularly limited, but may be, for example, Saccharomyces cerevisae ATCC 18824, ATCC 9763,ATCC 26615, ATCC 15248, IFO 555 and the like, Acetobacter xylinum IFO 3288, ATCC 10821, ATCC 31174, or Acetobacter pasteurianus ATCC 23766, Acetobocter rancens ATCC 23765, Sarcina ventriculi, Bacterium xyloides, Pseudomonas bacteria, Agrobacterium, Basidiomycetes such as Eubasidiomycetes.

Although the culture medium used to culture the microbe differs depending on the types of the water-insoluble glucan producing or constituting microbe (acetic acid bacteria, yeast, Basidiomycete), a culture medium normally used for those microbes in this field is used. The culture may be either a chemically defined medium or a natural medium, and a liquid medium is preferred. Exemplified for the chemically defined medium are various sugars as carbon sources; urea, ammonium salts, nitrates as a nitrogen sources; various vitamins, nucleotides, inorganic salts (Mg, Ca, Fe, Na, K, Mn, Co, Cu and the like) are exemplified. Exemplified for the natural culture are various sugars, amino acids, organic acids as carbon sources; soybean protein, protein hydrolysates, yeast extracts, meat extracts as nitrogen sources. The culture solution is preferably weak acidic and, normally pH 5.0–6.5. The culture temperature and time are, for example, 20°–25° C. and 24–216 hours.

Culture may be performed by any of ventilated-stirred culture, stationary culture, or solid culture.

The microbe cell-containing solution or the culture solution obtained through the aforementioned microbe culture normally has a microbe content of $2.0 \times 10^6 - 4.0 \times 10^9$ individuals/mL, a viscosity of 400–10,000 cp, and a degree of coloration (absorbance at 430 nm) of 0.4–7.0.

The culture solution or the microbe cell-containing solution may be diluted with water or the like and subjected to a hydroxide and an oxide described below. A treatment amount of the culture solution or the microbe cell-containing solution combined with an hydroxide and an oxide may be by diluting the culture solution or the microbe cell-containing solution by 1 to 10 folds, thereby achieving the advantages of the present invention. This manner maintains the uniformity during treatment, and prevents the oxide to react locally and non-uniformly. If an initial treatment solution of the culture solution or the microbe cell-containing solution combined with the hydroxide and the oxide has a microbe content greater than $4.0 \times 10^9$ individuals/mL, or a viscosity greater than 10,000 cp, or a coloration degree (absorbance at 430 nm) greater than 7.0, some substances will remain unreacted, which are not desirable. In such a case, it is necessary to dilute the treatment solution

3

In the water-insoluble glucan purification method of the present invention, a hydroxide and an oxide are added, to predetermined concentrations, to the microbe cell-containing solution or the culture solution obtained from the aforementioned microbe culture, and the mixture is stirred at 50°–70° C., preferably, 55°–65° C., for 8–24 hours, preferably, 14–18 hours.

As the hydroxide which uses for purification method of the present invention, sodium hydroxide, potassium hydroxide, calcium hydroxide, ammonium hydroxide, sodium hydrogen carbonate, or the like.

The hydroxide is added to the microbe cell-containing solution or the culture solution containing 0.1–10 wt.—wt. %, preferably, 0.5–3 wt.—wt. %, of water-insoluble glucan, so that the pH value becomes 10–12.5, preferably, 10.2–12.2.

If the hydroxide is added in such a manner that the pH value becomes less than 10, the viscosity of the treatment solution, the destruction of microbe cells and the coloration degree are not so much improved as in the present invention. If the pH value is greater than pH 12.5, the improvement of the coloration degree is reduced.

The oxide to be used in the purification method of the present invention may be, for example, peroxides, chlorine-base oxides, or the like.

Specific examples of the peroxides hydrogen peroxide, sodium peroxide, and the like. Specific examples of the chlorine-base oxides are chlorinated lime, sodium chlorite, sodium hypochlorite, and the like.

The oxide is added to the culture solution or the microbe cell-containing solution, to a concentration of substantially 0.175–3.5 wt.—wt. %, preferably, 0.175–3.0 wt.—wt. %.

If the oxide concentration is less than 0.175 wt.—wt.%, the decolorization becomes insufficient. If it exceeds 3.5 wt.—wt. %, different coloration will be observed, or other undesired results will occur.

The manner of adding the hydroxide and the oxide according to the purification method of the present invention is not particularly limited. More specifically, the hydroxide may be added before the oxide is added, or the oxide may be added before the hydroxide is added. Further, the hydroxide and the oxide may be added simultaneously or alternately. However, it is preferred to maintain the temperature of the reaction solution at 30° C. or lower during addition of the hydroxide and the oxide. Raising the temperature of the reaction solution, if needed, is preferably performed after the entire amounts of hydroxide and the oxide are added. Rapid addition of the hydroxide or the oxide will cause rapid and sudden production of oxygen or ammonium gas or the like, reducing the advantages of the present invention.

In the culture solution of the microbe cell-containing solution obtained through the purification steps described above, the number of normal cells is reduced at least to $1/5 \times 10^{-5}$ or less, and the coloration degree is reduced to $1/1.3 – 1/5$, and the viscosity is reduced to $1/1.7 – 1/10$, compared with those values before the treatment.

The aforementioned number of normal cells refers to the number of cells that remains unbroken although most microbes in the microbe cell-containing solution or the culture solution obtained through the microbe culture are destroyed by the hydroxide or the oxide. The number does not concern whether cells are dead or alive, but refers to the number of cells that retain the cell form.

The following table shows the improvements in the liquid properties of the culture solution of the microbe cell-containing solution achieved by the above-described purification method of the present invention.

TABLE 1

| Treatment | Viscosity[1] | Cell destruction[2] | Coloration[3] |
|---|---|---|---|
| Untreated | +++ | – | +++ |
| Treated with hydroxide | + | ++ | ++++ |
| Treated with oxide | ++ | + | + |
| Treated with hydroxide and oxide | + | +++ | – |

[1]Viscosity: +++ (high), ++ (intermediate), + (low).
[2]Destruction of microbe cells: +++ (very effective), ++ (effective), + (slightly effective), – (ineffective).
[3]Coloration degree : ++++ (colored), ++ (slightly colored), + (decolored), – (sufficiently decolored)

PREFERRED EMBODIMENTS OF THE INVENTION

The present invention will be described with reference to examples. However, the invention is not limited to the examples.

[Example 1]

(Purification of Nata de Coco)

300 mL of a culture medium indicated in Table 2 was placed in a 1-liter glass jar fermenter, and sterilized by heating at 120° C. for 20 minutes in an autoclave. After being cooled, the culture medium was seeded with Acetobacter xylinum ATCC 31174, which was uniformly dispersed. Through stationary culture at 30° C. for 96 hours, a culture solution was obtained. The culture solution contained nata de coco at a concentration of 10 g/L [determined as cellulose by a method described in Manual of Analytical Chemistry, p.998 (Japanese Society for Analytical Chemistry, 1961)]. The number of normal cells was $1.3 \times 10^9$ cells /mL (determined by a Thoma hemocytometer), and the viscosity was 5000 cp (determined in a suspension obtained by uniformly suspending 10 g/L of nata de coco in water, by a Brookfield type viscometer), and the coloration degree was 0.92 (absorbance measured at 430 nm).

TABLE 2

| Medium | Composition |
|---|---|
| Fructose | 40 g/L |
| $(NH_4)_2SO_4$ | 3.3 g/L |
| $KH_2PO_4$ | 1.0 g/L |
| $MgSO_4$ | 0.25 g/L |
| CSL | 40 mL/L |
| Salt mixture[1] | 10 mL/L |
| Vitamin mixture[2] | 10 mL/L |
| pH 5.0 (NaOH) | |
| Sterilization: 120° C., 20 min. | |

[1]Salt mixture:
$FeSO_4 \cdot 7H_2O$   361 mg/L
$CaCl_2 \cdot 2H_2O$   1.47 mg/L

TABLE 2-continued

| | |
|---|---|
| NaMoO$_4 \cdot _{2H2}$O | 24.2 mg/L |
| ZnSO$_4 \cdot$ 7H$_2$O | 173 mg/L |
| MnSO$_4 \cdot$ 5H$_2$O | 139 mg/L |
| CuSO$_4 \cdot$ 5H$_2$O | 5 mg/L |

[2)]Vitamin mixture:

| | |
|---|---|
| inositol | 200 mg/L |
| nicotine acid | 40 g/L |
| pyridoxine hydrochloride | 40 g/L |
| thiamine hydrochloride | 40 g/L |
| calcium pantothenate | 20 g/L |
| riboflavin | 20 g/L |
| p-aminobenzoic acid | 20 g/L |
| folic acid | 200 γ/L |
| biotin | 200 γ/L |

1) Treating Method 1-A 100 mL of water was added to and uniformly dispersed in 100 mL of the aforementioned culture solution. Centrifugation of the dispersion followed by washing twice with an equal amount of water produced a crude nata de coco. After a 27% NaOH aqueous solution was added to and uniformly suspended in the crude nata de coco so that the pH value became 13, the suspension was stirred at 60° C. for 14 hours. The thus-treated material had a viscosity of 1580 cp (determined by a Brookfield type viscometer), 2 ×10$^5$/mL of normal cells (determined by a Thoma hemocytometer), and a coloration degree of 5.2 (absorbance measured at 430 nm). After the treatment, nata de coco was recovered by centrifugation and washed with 100 mL of water twice, thus producing 0.7 g (dry weight) of a purified nata de coco.

2) Treating Method 1-B

After a 27% NaOH aqueous solution and H$_2$O$_2$ was added to 100 mL of the culture solution so that the pH value became 12.2 and the H$_2$O$_2$ concentration became 0.35 wt.—wt. %, the solution was stirred at 60° C. for 4 hours. The treated material had a viscosity of 500 cp, and all the cells were destroyed, and the coloration degree was 0.3 (absorbance measured at 430 nm). After the treatment, nata de coco was recovered by centrifugation and washed with 100 mL of water twice, thus producing 0.96 g of a purified nata de coco.

Table 3 shows results of determination of the recovery, purity and coloration degree of the nata de coco by the forgoing treating methods.

TABLE 3

| Treating method | Recovery (%) | Purity (%) | Coloration Y[1)] | Coloration WB[2)] | Absorbance at 430 nm |
|---|---|---|---|---|---|
| 1-A | 94 | 62 | 8.54 | 18.9 | 5.2 |
| 1-B | 96 | 98 | -18.9 | 32.4 | 0.3 |

[1)]Y was measured using a color-difference meter Z-300A, by Nippon Denshoku Kougyo Kabushiki Gaisha. The values indicate yellow coloration degrees, where a positive value indicates a relatively dense tone and a negative value indicates a relatively faded tone.

[2)]W indicates the white brightness, where 0 indicates black and the white brightness increases as the value approaches 100. With the white color of the white standard plate determined as 100%, the white brightness of the samples (solid) was determined at a wavelength of 457 nm (according to Concerning Colors, and the Z-300 User's Manual, by Nippon Denshoku Kougyo Kabushiki Gaisha).

3) Treating Method 1-C

The aforementioned culture solution was treated under conditions shown in FIG. 4, which also show the results.

| | Treated at 60° C. for 3 hrs. | | | | Treated at 60° C. for 4 hrs. | | | | Coloration after 3-day storage | |
|---|---|---|---|---|---|---|---|---|---|---|
| Treating condition | Viscosity (cp) | Number of normal cells (/mL) | Coloration Y[1)] | WB[2)] | Viscosity (cp) | Number of normal cells (/mL) | Y[1)] | WB[2)] | Y[1)] | WB[2)] |
| 0.70 w/w % H$_2$O$_2$ pH10.5 | 2600 | 1.5 × 10$^3$ | -4.7 | 30 | 2500 | 1.5 × 10$^3$ | -4.8 | 32 | -10 | 60 |
| 0.35 w/w % H$_2$O$_2$ pH12.2 | 2300 | 1.2 × 10$^2$ | -4.8 | 30 | 2200 | 1.2 × 10$^2$ | -4.8 | 30 | -15 | 58 |
| 0.70 w/w % H$_2$O$_2$ pH12.0 | 2200 | 1.0 × 10$^2$ | -4.8 | 30 | 2200 | 1.0 × 10$^2$ | -4.9 | 30 | -15 | 60 |
| 1.75 w/w % H$_2$O$_2$ pH11.9 | 2000 | 0 | -7.2 | 32 | 2000 | 0 | -8.5 | 35 | -15 | 62 |
| 0.70 w/w %H$_2$O$_2$ pH 9.5 | 2700 | 1.2 × 10$^9$ | -3.4 | 17 | 2700 | 1.2 × 10$^9$ | -3.3 | 17 | -1.5 | 18 |
| 0% H$_2$O$_2$ pH13.0 | 2700 | 1.0 × 10$^8$ | 10.2 | 4 | 2700 | 1.2 × 10$^7$ | 10.2 | 4 | 10.2 | 4 |
| Untreated [ 0% H$_2$O$_2$ pH 5.5 ] | 2700 | 1.3 × 10$^9$ | 3.2 | 13 | 2700 | 1.3 × 10$^9$ | 3.2 | 13 | 3.2 | 13 |

[1),2)]: the same as in Table 3.

[EXAMPLE 2]

(Purification of Bacterial cellulose)

Acetobactor xylinum ATCC 31174 was cultured in a culture medium as in Example 1 while being stirred and ventilated, to obtain a culture solution. The culture solution contained bacterial cellulose at a concentration of 15 g/L [determined as cellulose by the method described in Manual of Analytical Chemistry, p.998 (Japanese Society for Analytical Chemistry, 1961)]. The number of normal cells was 1.3×10$^9$ cells/mL (determined by a Thoma hemocytometer), and the viscosity was 5000 cp (measured by a Brookfield type viscometer), and the coloration degree was 0.92 (absorbance measured at 430 nm).

After 100 mL of water was added to and uniformly dispersed in 100 mL of the culture solution, a 27% NaOH aqueous solution and, also, H$_2$O$_2$ were added to samples so that the pH values became 10.5, 12.0 and 12.5 and the H$_2$O$_2$ concentrations became 0.175 wt.—wt. %, 0.7 wt.—wt. % and1.05 wt.—wt. %, respectively (Treating Methods 2-A to 2-I). After being uniformly suspended, the suspension was stirred at 60° C. for 4 hours. Likewise, a 27% NaOH aqueous solution was added to a sample so that the pH value became 12.0 (Treating Method 2-J) and, $H_2O_2$ was added to a sample so that the $H_2O_2$ concentration became 1.05 wt.—wt. %. The samples were similarly treated. The results of analyses of the treated materials are shown in Table 5.

TABLE 5

| Treating method | Treating conditions | | Viscosity (cp) | No. of normal cells (/mL) | Coloration (absorbance at 430 nm) |
|---|---|---|---|---|---|
| | pH | $H_2O_2$ conc. | | | |
| 2-A | 10.3 | 0.175 w % | 2900 | $2.6 \times 10^3$ | 0.40 |
| 2-B | 10.5 | 0.7 w % | 2500 | $1.5 \times 10^3$ | 0.35 |
| 2-C | 10.0 | 1.05 w % | 2000 | $1.2 \times 10^3$ | 0.32 |
| 2-D | 12.3 | 0.175 w % | 2700 | $1.8 \times 10^2$ | 0.50 |
| 2-E | 12.0 | 0.7 w % | 2200 | $1.0 \times 10^2$ | 0.45 |
| 2-F | 11.8 | 1.05 w % | 2000 | 0 | 0.42 |
| 2-G | 12.5 | 0.175 w % | 620 | 0 | 0.70 |
| 2-H | 12.4 | 0.7 w % | 550 | 0 | 0.50 |
| 2-I | 12.3 | 1.05 w % | 500 | 0 | 0.30 |
| 2-J | 12.0 | — | 2000 | $2.3 \times 10^5$ | 5.20 |
| 2-K | 5.5 | 1.05 w % | 5000 | $1.4 \times 10^9$ | 0.46 |
| 2-L | Untreated (pH 5.5) | | 5000 | $1.3 \times 10^9$ | 0.92 |

After the treatments shown in Table 5, bacterial cellulose was recovered by centrifugation and washed with 100 mL of water three times, thus producing crude bacterial cellulose. The recovery, purity and coloration according to the different treatments are shown in Table 6.

TABLE 6

| Treating method | Recovery (%) | Purity (%) | Coloration | |
|---|---|---|---|---|
| | | | $Y^{1)}$ | $WB^{2)}$ |
| 2-A | 96 | 80 | −4.1 | 35 |
| 2-B | 95 | 88 | −7.6 | 32 |
| 2-C | 96 | 89 | −10.2 | 30 |
| 2-D | 96 | 89 | −3.6 | 27 |
| 2-E | 95 | 90 | −4.9 | 30 |
| 2-F | 97 | 99 | −8.5 | 35 |
| 2-G | 96 | 98 | −6.2 | 32 |
| 2-H | 95 | 98 | −7.8 | 34 |
| 2-I | 96 | 99 | −10.2 | 36 |
| 2-J | 94 | 70 | 9.2 | 5 |
| 2-K | 95 | 72 | −3.4 | 17 |
| 2-L | 96 | 63 | 3.2 | 13 |

$^{1)}$, $^{2)}$:the same as in Table 3.

[EXAMPLE 3]

(Purification of Bacterial cellulose)

The culture solution of Acetobactor xylinum obtained by substantially the same method as in Example 2 was treated at 60° C. for 4 hours under the conditions (3-A to 3-I), (3'-A to 3'-I) shown in Tables 7 and 8.

TABLE 7

| Treating method | Treating conditions | Viscosity (cp) | No. of normal cells (/mL) | Coloration (absorbance at 430 nm) |
|---|---|---|---|---|
| 3-A | pH 12.3 <KOH> 1.05 w % $H_2O_2$ | 452 | 0 | 0.32 |

TABLE 7-continued

| Treating method | Treating conditions | Viscosity (cp) | No. of normal cells (/mL) | Coloration (absorbance at 430 nm) |
|---|---|---|---|---|
| 3-B | pH 12.3 <NH$_4$OH> 1.05 w % $H_2O_2$ | 460 | 0 | 0.25 |
| 3-C | pH 12.3 <NaHCO$_3$> 1.05 w % $H_2O_2$ | 500 | 0 | 0.30 |
| 3-D | pH 13 <KOH> | 2450 | $2.2 \times 10^5$ | 4.98 |
| 3-E | pH 13 <NH$_4$OH> | 2620 | $2.0 \times 10^5$ | 5.32 |
| 3-F | pH 13 <NaHCO$_3$> | 2800 | $4.3 \times 10^5$ | 3.20 |
| 3-G | pH 13 <NaOH> | 2500 | $2.3 \times 10^5$ | 5.20 |
| 3-H | 1.05 w % $H_2O_2$ (pH 5.5) | 5000 | $1.2 \times 10^9$ | 0.46 |
| 3-I | Untreated (pH 5.5) | 5000 | $1.3 \times 10^9$ | 0.92 |

TABLE 8

| Treatment sample | Treating conditions | Viscosity (cp) | No. of normal cells (/mL) | Coloration (absorbance at 430 nm) |
|---|---|---|---|---|
| 3'-A | pH 12.0 <NaOH> 3% NaOCl | 480 | 0 | 0.31 |
| 3'-B | pH 12.0 <NaOH> 3% chlorinated lime | 510 | 0 | 0.33 |
| 3'-C | pH 12.0 <NaOH> 3% sodium chlorite | 500 | 0 | 0.42 |
| 3'-D | 3% NaOCl (pH 5.5) | 5100 | $1.0 \times 10^9$ | 0.55 |
| 3'-E | 3% chlorinated lime (pH 5.5) | 5300 | $1.4 \times 10^9$ | 0.54 0 |
| 3'-F | 3% sodium chlorite (pH 5.5) | 5000 | $1.1 \times 10^9$ | 0.62 |
| 3'-G | pH 12.0 <NaOH> | 2500 | $2.3 \times 10^9$ | 5.20 |
| 3'-H | Untreated (pH 5.5) | 5000 | $1.3 \times 10^9$ | 0.92 |

After the treatments shown in Tables 7 and 8, bacterial cellulose was recovered by centrifugation and washed with 100 mL of water three times, thus producing purified bacterial cellulose. The treatment samples 3-A to 3-C in Table 7 and 3'-A to 3'-C in Table 8 had purities of 99% or higher. On the other hands, the control samples (treatment samples 3-D to 3-H in Table 7 and 3'-D to 3'-G in Table 8), and the untreated samples (treatment sample 3-I in Table 7 and treatment sample 3'-H in Table 8) had purities of 70% or lower.

[EXAMPLE 4]

(Purification of Yeast Glucan)

After a culture medium containing 50 g/L of glucose, 3 g/L of ammonium sulfate, 2 g/L of yeast extract, 2 g/L of peptone, 10 g/L of monopotassium phosphate, 2 g/L of magnesium sulfate, 0.7 g/L of calcium chloride was adjusted to pH 5.5 with sulfuric acid, 300 mL of the culture solution was placed in a 1-liter glass jar fermenter and sterilized by heating at 120° C. for 20 minutes in an autoclave. After being cooled, the culture medium was seeded with Saccharomyces cerevisiae IFO 555. Through stirred and ventilated culture at 30° C. for 30 hours, a culture solution was obtained. A 27% NaOH aqueous solution was added to 100 mL of the culture solution so that the pH value became 12, and then the solution was treated at 70° C. for 4 hours (4-A). A 27% NaOH aqueous solution and $H_2O_2$ were added to 100 mL of the culture solution so that the pH value became 12 and the $H_2O_2$ concentration became 0.35 wt.—wt. %, and then the solution was treated at 70° C. for 4 hours (4-B). The viscosity, the number of remaining normal cells and the coloration of the culture solutions were determined. The viscosities of the culture solutions 4-A and 4-B were 420 cp and 95 cp, respectively. The numbers of normal cells of the culture solutions 4-A and 4-B were $2.6\times10^7$ cells/mL and $1.2\times10^5$ cells/mL or lower, respectively. The coloration degrees (absorbance at 430 nm) of the culture solutions 4-A and 4-B were 0.85 and 0.1, respectively.

The materials treated by the treating methods 4-A and 4-B were washed with 100 mL of water six times, and then freeze-dried. The dried materials obtained were 0.5 g for 4-A and 0.12 g for 4-B. The materials were hydrolyzed qt 100° C. for 8 hours by 2N sulfuric acid. The released glucose was analyzed for purity of yeast glucan by a glucose analyzer. The results were 48% for 4-A and 85% for 4-B.

[EXAMPLE 5]

(Purification of Lenthinan)

An aqueous solution was obtained by adding 27% NaOH aqueous solution to 300 g of a mushroom (Lentinus edodes) so that the pH value became 12, and then treated at 60° C. for 4 hours (5-A). Another aqueous solution was obtained by adding 27% NaOH aqueous solution and $H_2O_2$ to 300 g of a mushroom (Lentinus edodes) so that the pH value became 12 and the $H_2O_2$ concentration became 0.35 wt.—wt. %, and then treated at 60° C. for 4 hours (5-B). The viscosity, the condition of cell destruction and coloration of the solutions were determined. The results are shown in Table 9.

TABLE 9

|     | Viscosity (cp) | Condition of cell destruction* | Coloration (absorbance at 430 nm) |
| --- | --- | --- | --- |
| 5-A | 4800 | + | 1.2 |
| 5-B | 500 | +++ | 0.3 |

*)The shape of cells was observed under a microscope. No deformation is indicated by −; at most 10% deformation by +; 10–50% deformation by ++; 50% or greater deformation by +++.

After the solutions were centrifuged to remove impurities, the materials were washed with water six times. Freeze-dried materials obtained were 1.8 g for 5-A and 0.3 g for B-4.

Samples of 10 mg were taken from the obtained materials, and uniformly suspended in 2mL of 2 N $H_2SO_4$. After the suspensions were subjected hydrolysis at 100° C. for 8 hours, the released glucose was analyzed by a glucose analyzer for comparison in purity. The results were 32% for 5-A and 80% for 5-B.

EFFECT OF THE INVENTION

Since the present invention accomplishes all of the destruction of production microbe, the decolorization and the reduction of viscosity of a culture solution of a microbe that produces water-insoluble glucan or a microbe cell-containing solution comprising water-insoluble glucan as a component, the invention purifies water-insoluble glucan industrially at low costs and with a high efficiency.

What is claimed is:

1. A water-insoluble glucan purification method wherein a culture solution of a microbe that produces water-insoluble glucan or a microbial cell-containing solution comprising water-insoluble glucan as a component is treated with both an oxide of 0.175–3.5 wt.—wt. % and a hydroxide such that the pH value becomes 10–12.5.

2. A water-insoluble glucan purification method according to claim 1, wherein the water-insoluble glucan is selected from lenthinan, yeast glucan or cellulose.

3. A water-insoluble glucan purification method according to claim 1, wherein the content of microbe of the culture fluid or the microbial cell-containing solution is $2.0\times10^6$–$4.0\times10^9$ individuals/mL.

4. A water-insoluble glucan purification method according to claim 1, wherein the viscosity of the culture fluid or the microbial cell-containing solution is 400–10,000 cps.

* * * * *